(12) United States Patent
Boutoussov

(10) Patent No.: US 7,563,226 B2
(45) Date of Patent: Jul. 21, 2009

(54) HANDPIECES HAVING ILLUMINATION AND LASER OUTPUTS

(75) Inventor: Dmitri Boutoussov, Dana Point, CA (US)

(73) Assignee: Biolase Technology, Inc., Irvine, CA (US)

( * ) Notice: Subject to any disclaimer, the term of this patent is extended or adjusted under 35 U.S.C. 154(b) by 97 days.

(21) Appl. No.: 11/033,031

(22) Filed: Jan. 10, 2005

(65) Prior Publication Data
US 2005/0256516 A1 Nov. 17, 2005

Related U.S. Application Data

(60) Provisional application No. 60/535,183, filed on Jan. 8, 2004.

(51) Int. Cl.
*A61B 1/04* (2006.01)
*A61B 1/06* (2006.01)
*A61B 18/18* (2006.01)

(52) U.S. Cl. .................. 600/108; 600/182; 606/15; 606/18

(58) Field of Classification Search .............. 600/108, 600/156, 158, 182, 342; 606/2, 13–18, 46; 607/89–94
See application file for complete search history.

(56) References Cited

U.S. PATENT DOCUMENTS

| | | | |
|---|---|---|---|
| 4,445,892 A | | 5/1984 | Hussein et al. |
| 4,770,653 A | * | 9/1988 | Shturman ................... 606/7 |
| 4,787,370 A | * | 11/1988 | Kanamori ................ 600/175 |
| 4,913,142 A | | 4/1990 | Kittrell et al. |
| 4,931,047 A | | 6/1990 | Broadwin et al. |
| 4,985,027 A | | 1/1991 | Dressel |
| 5,051,823 A | | 9/1991 | Cooper et al. |
| 5,102,410 A | | 4/1992 | Dressel |
| 5,196,004 A | | 3/1993 | Sinofsky |
| 5,263,950 A | | 11/1993 | L'Esperance, Jr. |
| 5,267,856 A | | 12/1993 | Wolbarsht et al. |
| 5,395,362 A | * | 3/1995 | Sacharoff et al. ........... 600/108 |

(Continued)

FOREIGN PATENT DOCUMENTS

DE 19510939 A1 9/1996

(Continued)

OTHER PUBLICATIONS

International Search Report & Written Opinion, May 23, 2007, PCT/US05/00756.

(Continued)

*Primary Examiner*—John P Leubecker
*Assistant Examiner*—Philip R Smith
(74) *Attorney, Agent, or Firm*—Stout, Uxa, Buyan & Mullins, LLP

(57) ABSTRACT

An illumination device for medical and dental procedures is described. The illumination device includes an elongate body configured to contain two or more optical fibers to transmit electromagnetic energy from a power source toward a target surface. The distal end of the illumination device is illustrated as a unitary structure, and the proximal end is illustrated as having multiple proximal end members. The illumination device includes two or more optical fibers for transmitting energy toward the distal end, and at least one optical fiber for transmitting energy from the distal end toward the proximal end of the device.

21 Claims, 4 Drawing Sheets

U.S. PATENT DOCUMENTS

| | | | |
|---|---|---|---|
| 5,402,770 A * | 4/1995 | Iida et al. .................... 600/159 |
| 5,540,683 A | 7/1996 | Ichikawa et al. |
| 5,741,247 A | 4/1998 | Rizoiu et al. |
| 5,785,521 A | 7/1998 | Rizoiu et al. |
| 5,825,958 A | 10/1998 | Gollihar et al. |
| 5,836,941 A * | 11/1998 | Yoshihara et al. ............. 606/15 |
| 6,106,516 A | 8/2000 | Massengill |
| 6,118,521 A | 9/2000 | Jung et al. |
| 6,254,597 B1 | 7/2001 | Rizoiu et al. |
| 6,325,794 B1 * | 12/2001 | Yoon et al. .................... 606/17 |
| 6,389,193 B1 | 5/2002 | Kimmel et al. |
| 6,464,689 B1 | 10/2002 | Qin et al. |
| 6,669,685 B1 | 12/2003 | Rizoiu et al. |
| 2003/0018325 A1 * | 1/2003 | Sakaguchi et al. ............ 606/10 |
| 2003/0032862 A1 * | 2/2003 | Ota et al. .................... 600/158 |
| 2003/0045780 A1 * | 3/2003 | Utsui ........................ 600/182 |
| 2003/0167066 A1 | 9/2003 | Trout, III et al. |
| 2004/0030326 A1 * | 2/2004 | Altshuler et al. .............. 606/10 |
| 2004/0102767 A1 * | 5/2004 | Stingl et al. .................... 606/11 |
| 2004/0106081 A1 | 6/2004 | Karazivan et al. |
| 2005/0080404 A1 * | 4/2005 | Jones et al. .................... 606/16 |
| 2006/0127861 A1 * | 6/2006 | Villoresi et al. ............. 433/215 |

FOREIGN PATENT DOCUMENTS

| | | |
|---|---|---|
| EP | 0654251 A | 5/1995 |
| GB | 2369057 | 5/2002 |
| JP | 2003001465 | 1/2003 |
| WO | 09 07928 | 3/1997 |
| WO | WO 02/098315 | 12/2002 |
| WO | 2005/070129 | 8/2005 |

OTHER PUBLICATIONS

Webb et al., "Wavelength-Resolved 3-Dimensional Fluorescence Lifetime Imaging", Journal of Fluorescence, vol. 12, No. 2, Jun. 2002, pp. 296-283.

* cited by examiner

HANDPIECES HAVING ILLUMINATION AND LASER OUTPUTS

CROSS-REFERENCE TO RELATED APPLICATIONS

This application claims the benefit of U.S. Provisional Application No. 60/535,183, filed Jan. 8, 2004 and entitled ILLUMINATION DEVICE AND RELATED METHODS, the contents of which are expressly incorporated herein by reference. This application is related to U.S. application Ser. No. 11/186,409, filed Jul. 20, 2005 and entitled CONTRA-ANGLE ROTATING HANDPIECE HAVING TACTILE-FEEDBACK TIP FERRULE, and U.S. application Ser. No. 11/186,619, filed Jul. 20, 2005 and entitled CONTRA-ANGLE ROTATING HANDPIECE HAVING TACTILE-FEEDBACK TIP FERRULE.

BACKGROUND OF THE INVENTION

1. Field of the Invention

The present invention relates to illumination devices, and more particularly to illumination devices used in connection with medical and dental settings. More specifically, the present invention relates to an illumination device including a plurality of fibers that transmit and emit electromagnetic energy, such as light, toward a target surface. The fibers of the device are configured to deliver cutting energy, light for illumination of an operational area, light for excitation of the target surface and/or curing energy to the target surface, and to transmit light from the target surface back to one or more analyzers.

2. Description of Related Art

Optical cutters are well-known in medical, dental, and industrial settings. Generally, optical cutters employ a source of electromagnetic energy, such as a laser source, and an optical fiber system connected to the laser source and configured to direct the laser through one or more optical fibers to a surface to be cut. The optical fiber system may include one or more optical fibers contained within an optical fiber tube. The optical fiber tube may have a device at its end (the distal end) for controlling the delivery of the laser to the surface to be cut. The other end (the proximal end) of the optical fiber tube is connected or coupled to the laser source.

SUMMARY OF THE INVENTION

The present invention herein disclosed relates to an illumination device having a plurality of optical fibers which transmit electromagnetic energy toward a target surface for medical and dental procedures. An illumination device in accordance with the invention herein disclosed includes an elongate body that has a distal end and a proximal end, and a hollow interior. Two or more optical fibers, or other light transmitters, are located in the hollow interior of the elongate body.

In one embodiment, the illumination device includes an elongate body with at least two proximal end members, each proximal end member having a hollow interior sized to accommodate at least one light transmitter, and in communication with a hollow interior of the elongate body so that the at least one light transmitter extends from the proximal end to the distal end of the elongate body. In the illustrated embodiment, the illumination device includes four proximal end members. Three of the proximal end members may have equally sized inner diameters, and a fourth proximal end member may have a diameter that is less than the diameter of the other three members.

In another embodiment, an illumination device includes a distal portion and a proximal portion. The distal portion of the elongate body includes a unitary distal portion tube which includes a lumen extending therethrough. The proximal portion includes a plurality of proximal portion tubes, each proximal portion tube having a lumen in communication with the lumen of the distal portion of the elongate body. In the illustrated embodiments, the distal portion and proximal portion of the elongate body are integrally formed. The illumination device is illustrated as having four proximal portion tubes, where three of the four proximal portion tubes have similar diameters.

In certain embodiments of the foregoing device, the first, second and third proximal portion tubes each contain three optical fibers disposed in the lumens of the proximal portion tubes, and the fourth proximal portion tube contains one optical fiber disposed in the fourth proximal portion tube lumen. The optical fibers may be fused or separate from each other. At least a portion of the elongate body is flexible, such as a major portion of the elongate body. In certain embodiments, the distal portion of the elongate body includes a region that is rigid, straight and axially symmetrical relative to the proximal portion of the elongate body.

The illumination device of the present invention includes a light emitting output end, and it may also include at least one mirror or other reflector distally located to the light emitting output end. In one embodiment, the illumination device includes two mirrors near the output end, one mirror being constructed to reflect electromagnetic energy provided by an erbium cutting laser, and a second mirror constructed to reflect visible light. The device may include a hand piece sized to be held by a user's hand. The hand piece is typically coupled to the distal end of the elongate body of the illumination device, and may include the reflectors, as discussed herein.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

BRIEF DESCRIPTION OF THE DRAWINGS

FIG. 1A is a sectional view along line 1A-1A of FIG. 1.

FIG. 1B is a sectional view along line 1B-1B of FIG. 1.

FIG. 1C is a sectional view along line 1C-1C of FIG. 1.

FIG. 3A is a sectional view along line 3A-3A of FIG. 3.

FIG. 3B is a sectional view along line 3B-3B of FIG. 3.

DETAILED DESCRIPTION OF THE PRESENTLY PREFERRED EMBODIMENTS

Figure 1:
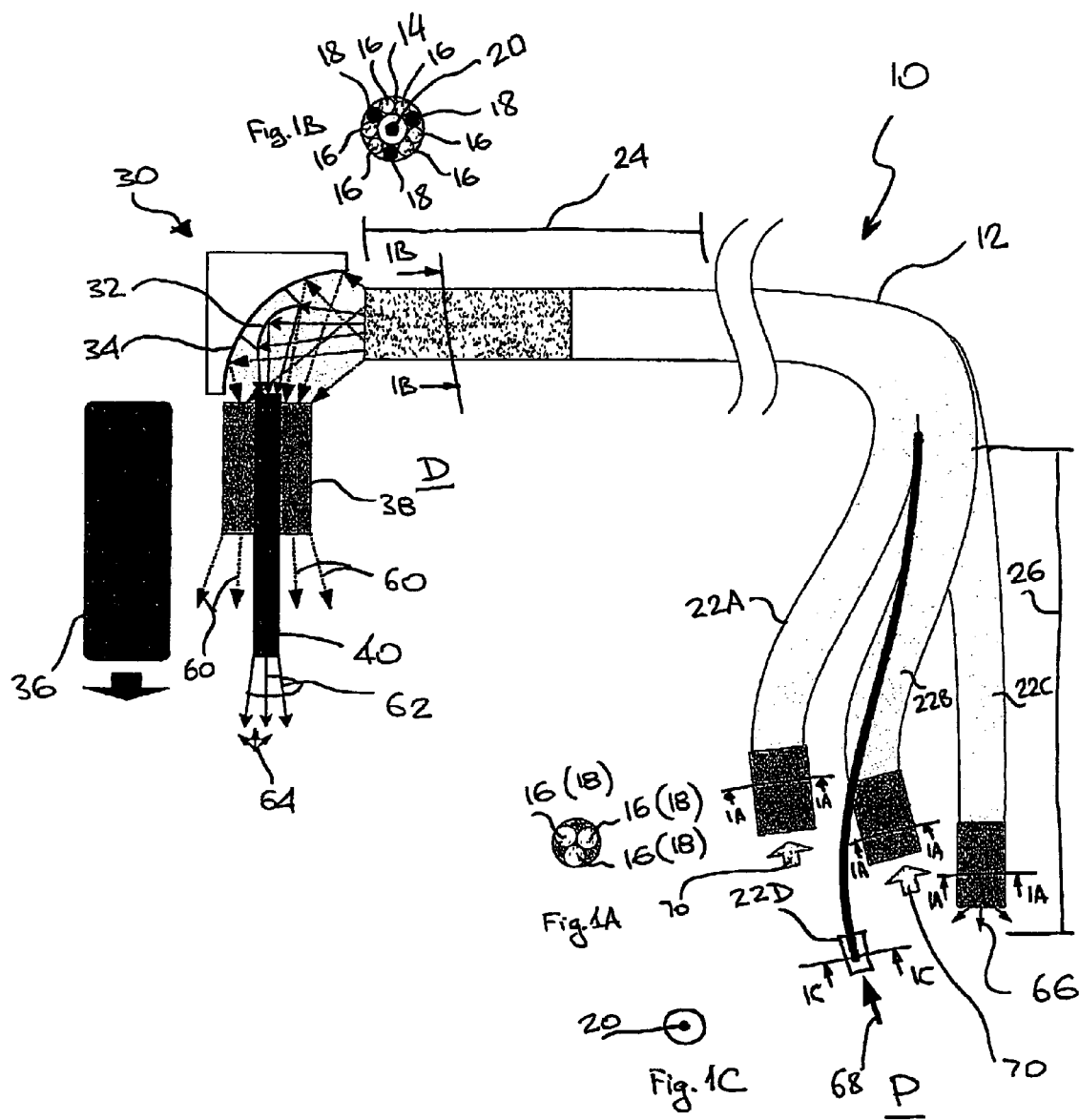
FIG. 1 is a side elevation view of a illumination device of the invention.

The present invention disclosed herein relates to illumination devices which utilize optical fibers to transmit electromagnetic energy toward a target surface. As used herein, "optical fiber" refers to any light transmitting fiber that is able to transmit light from one end of the fiber to another end of the fiber. The light transmission may be passive or it may include one or more light altering elements to influence the way light is emitted from the optical fiber. Optical fibers can be used to transmit any type of light, including, visible light, infrared light, blue light, laser light, and the like. Optical fibers may be hollow or solid, and may include one or more reflectors within the fiber bodies to control transmission and emission of light from the optical fibers.

An illumination device in accordance with the present invention includes a unitary distal end (output end) and a split proximal end (input end). As used herein, "distal end" refers to the end of an illumination device that is closest to a target surface, and "proximal end" refers to the end of an illumination device that is closest to a power source, or other source of electromagnetic energy. The illumination device can include a plurality of different sized optical fibers depending on the particular application for which the illumination device is utilized. In the illustrated embodiment, and as disclosed herein, the proximal end of the illumination device includes four proximal end members configured to accommodate four sets of optical fibers.

Another illumination device in accordance with the present invention includes a plurality of optical fibers configured to emit electromagnetic energy from the distal end of the illumination device toward a target surface, and at least one optical fiber configured to receive electromagnetic energy from the target surface and transmit it to the proximal end of the illumination device. The electromagnetic energy that is transmitted to the proximal end of the illumination device can be used as a signal for further analysis.

In another embodiment of the present invention, an illumination device includes a hand piece having a reflector. The reflector is constructed to reflect both laser energy, such as light provided by an erbium laser, and visible light, including blue light, toward a target surface. It also reflects light from target surface towards proximal end of illumination device. In the illustrated embodiment, as disclosed herein, the reflector includes a plurality of mirrors to provide enhanced control of the emission of electromagnetic energy from the optical fibers toward a target surface and back.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, front, distal, and proximal are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. The present invention may be utilized in conjunction with various medical and/or dental procedures that are conventionally used in the art.

Referring to the figures, and specifically FIG. 1, an illumination device 10 is illustrated. Illumination device 10 includes an elongate body 12 having a generally tube-like structure that is structured to contain a plurality of light transmitters, such as optical fibers and the like, which are used to transmit light toward or from a hand piece. In the illustrated embodiment, illumination device 10 includes an elongate body 12 surrounding a hollow interior 14 (see FIG. 1B). Illumination device 10 has a distal end D and a proximal end P, the distal end being the end closest to the end being held by a user. Referring to the illustrated embodiment, a distal portion 24 of illumination device 10 includes distal end D, and a proximal portion 26 includes proximal end P. Elongate body 12 is a hollow structure having a portion that is flexible, and a portion that may be substantially inflexible. Referring to the apparatus of FIG. 1, a fraction of distal portion 24 is substantially inflexible, or is generally rigid and straight, and a fraction of elongate body, including proximal portion 26 is flexible. In additional embodiments, both distal portion 24 and proximal portion 26 are flexible. Elongate body 12 can be made from any suitable material or materials, such as stainless steel, metal coil or plastic. In addition, apparatus 10 is illustrated as having a generally cylindrical cross-section, but it could also include one or more portions with different cross-sectional shapes including oval, rectangular, or triangular, and the like.

Illumination device 10 is illustrated having a plurality of proximal members 22A, 22B, 22C and 22D. Each proximal member 22A, 22B, 22C and 22D has a hollow interior configured to accommodate one or more light transmitters or other tubular or elongate structures that have cross-sectional areas less than the cross-sectional area of the hollow interior. Proximal members 22A, 22B, 22C and 22D are arranged such that the hollow interiors of each of the proximal members is in communication with hollow interior 14 of elongate body 12. This arrangement provides for a substantially continuous path for the light transmitters to extend from proximal end P to distal end D of elongate body 12. Although the illustrated embodiment is provided with four proximal members, additional embodiments could be provided with two, or three or more proximal members, depending on for example the number of light transmitters being used in the apparatus. In addition, the illustrated embodiment of illumination device 10 includes two proximal members 22A, and 22B that have substantially equal diameters, and one proximal member 22C that may have a diameter that is different than either of the diameters of the other two proximal members. Other diameter distributions among the four proximal members may be implemented in modified embodiments. According to the example embodiment illustrated in FIG. 1, proximal member 22D has a fiber 20 for transmitting cutting laser energy.

Illumination device 10 is illustrated as being configured to be held by a user. In a preferred embodiment, illumination device 10 is configured to direct electromagnetic energy from a hand piece and/or receive energy that may be generated in proximity to the hand piece. The illumination device can be used in medical, industrial, dental, and other applications. In one embodiment, the illumination device is a device for emitting electromagnetic energy in dental applications. The electromagnetic energy preferably includes light, such as visible light, laser light, and the like. The device can be used in dental hygiene procedures as well.

Illumination device 10 is typically connected to at least one external electromagnetic energy source, such as a laser, a light emitting diode (LED), and/or a lamp, so that the electromagnetic energy that is generated by the source can be transmitted through illumination device 10 and directed from a hand piece. In modified embodiments, the electromagnetic energy source and/or delivery system may comprise parts or substantially all of that described in U.S. Pat. No. 5,741,247 to the extent compatible; or, in other embodiments, structures described in the referenced patent may be modified to be compatible with the device 10.

In a further embodiment of the invention, and as illustrated in FIG. 1, the illumination device includes an elongate body 12 having a distal portion 24 and a proximal portion 26. Distal portion 24 is illustrated as being a unitary structure having an inner lumen to form a distal portion tube, and proximal portion 26 includes a plurality of proximal portion tubes 22A, 22B, 22C and 22D, each proximal portion tube having a lumen in communication with lumen 14 of distal portion 24.

Referring to elongate body 12 of FIG. 1, proximal members 22A, 22B, and 22C are integrally formed with distal portion 24 of the elongate body, and proximal member 22D is a separate element that is connected to elongate body 12, so that the proximal member lumens are in communication with the hollow interior or lumen 14 of distal portion 24. In additional embodiments, fewer (e.g., none) or greater numbers of separate elements can be joined or connected to elongate body 12.

In the illustrated embodiment of elongate body 12, distal end D includes an electromagnetic energy emitting output end, and proximal end P includes an electromagnetic energy input end. Referring to proximal members 22A, 22B, 22C and 22D of FIG. 1, each proximal member includes a lumen dimensioned to accommodate one or more light transmitters or other tube- or fiber-like structures. In the illustrated embodiment, proximal members 22A, 22B and 22C each contain three energy emitting fibers, such as optical fibers, and proximal member 22D contains one energy emitting fiber, such as an optical fiber. In modified embodiments, proximal member 22C may have a different cross-sectional area relative to, for example, one or both of the proximal members 22A and 22B. As shown in the illustrated embodiment of FIG. 1A, which is a sectional view along the line 1A-1A of FIG. 1, the three optical fibers 16, which are in each of the proximal members 22A and 22B, are bundled together. In other embodiments, the three optical fibers 16 within one or more of the proximal members can be substantially fused together or joined by other means to define a unitary light emitting assembly or waveguide.

In the illustrated example, proximal member 22C also includes three fibers 18, which are depicted in the sectional view of FIG. 1B that is taken along the line 1B-1B near distal end D of elongate body 12. Fibers 18, also indicated with parentheses in FIG. 1A as having a similar form and orientation as fibers 16, are in the illustrated embodiment equally separated from each other. In other embodiments, two or more of the fibers 18 can be positioned asymmetrically and/or fused or otherwise joined together. One or more of the fibers 18 may also be of different diameter than, for example, one or more of the fibers 16. Fibers 16 and 18 can be manufactured from plastic using conventional techniques, such as extrusion and the like.

Optical fiber 20 is illustrated as part of proximal member 22D passing between proximal members 22A and 22B near the input end of elongate body 12, and centrally disposed relative to fibers 16 and 18 near the output end of elongate body 12 (as shown in FIG. 1B). Optical fiber 20 is illustrated as a power erbium fiber that is structured to fit inside elongate body 12 but may comprise other structures in modified embodiments. At the output end, the fibers 16 and 18 are arranged in a plane. Preferably, the fibers are cut and polished in the same plane, and the fibers are arranged to be maintained in a substantially fixed position relative to one another and the hand piece. Fiber 20 may be polished and inserted separately, but mounted in a fixed position as well. For example, tubing, such as metal tubing, can be used both at the inside of elongate body 12 and outside of elongate body 12 to keep part, and preferably all, of the fibers 16, 18, and 20 in a fixed, straight position.

At the input end, or proximal end P, as illustrated in FIG. 1, fibers 16 of proximal members 22A and 22B are configured to receive and transmit light from for example a laser, an LED, or a lamp. As presently embodied, white light 70, for example white light generated by one or more white light LEDs is input. In the illustrated embodiment, two ultra-bright white light LEDs are used as a source of illumination light for transmission through fibers 16, with each LED generating, for example, electromagnetic energy at a power level of about 200 mW in either continuous wave (CW) or pulsed mode. In other embodiments, one or both white light LEDs can be substituted with different LEDs having different properties such as different colors (e.g., blue). Blue light can be particularly useful in curing dental composites, tooth whitening, and caries detection, among other things, when the device is used for dental care and hygiene. In this case, each proximal member 22A and 22B may include an optional shutter mechanism or filter (not shown) to influence the transmission of blue light from the LEDs. The shutter mechanism or filter might be structured to convert blue light into white, or any other visible light. This may be accomplished by using or placing phosphoric filters in front of each of the proximal members 22A and 22B.

Proximal member 22C is configured to accommodate the three fibers 18, as discussed above. In the illustrated embodiment, optical fibers 18 are configured to collect or receive reflected and scattered light from the output end of apparatus 10 and guide that light back toward the input end. The reflected and/or scattered light can be used as a feedback signal, which can be passed to a sensor or other suitable device for analysis as indicated by 66 in FIG. 1. The feedback signal can detect damage of an optical surface (e.g., aiming red light beam will scatter and reflect back), fluorescence of dental material (e.g., caries, bacteria, demineralization, and the like) among other things. An optical fiber for erbium radiation (at about a 3 micron wavelength range), or fibers for transmission of other laser radiation, 20 can be inserted into elongate body 12 such that the distal end of fiber 20 is parallel with fibers 16 and 18 at distal end D of apparatus 10. In the illustrated embodiment, fiber 20 is centrally disposed along a central longitudinal axis of elongate body 12, as shown in FIG. 1B. In the illustrated configuration, fibers 16 and 18 are perimetrically disposed around fiber 20, at least at the distal end D of apparatus 10. The concentric configuration of fibers 16, 18, and 20 can be maintained for any desired distance of elongate body 12, and in the illustrated embodiment, the concentric configuration is maintained until a region where proximal members 22A, 22B, and 22C split from elongate body 12.

At the output end of elongate body 12, light is emitted from and collected into illumination device 10. In the illustrated embodiment, light or other electromagnetic radiation is emitted from fibers 16, and light is collected by a transparent tip or other type of waveguides 38. In addition, light or other electromagnetic radiation from a laser, a LED, or a lamp can be emitted from fiber 20.

In an illustrated embodiment, electromagnetic radiation 68 is derived from an erbium, chromium, yttrium scandium gallium garnet (Er, Cr:YSGG) solid state laser, which generates electromagnetic energy having a wavelength of approximately 2.78 microns at an average power of up to 8 Watts, a repetition rate of about 10 to 50 Hz, and a pulse width of about 150 to 700 microseconds. Moreover, electromagnetic radiation 68 may further comprise an aiming beam, such as light having a wavelength of about 655 nm and an average power of about 1 mW (CW or pulsed mode). In one embodiment, blue or/and white light are emitted from one or more fibers 16, reflected light or stimulated fluorescent light is collected by fibers 18, and erbium laser light is emitted from fiber 20. The emitted light is directed toward a working surface, such as a tissue surface, including a surface of a tooth, to perform one or more light sensitive procedures.

Figure 2:
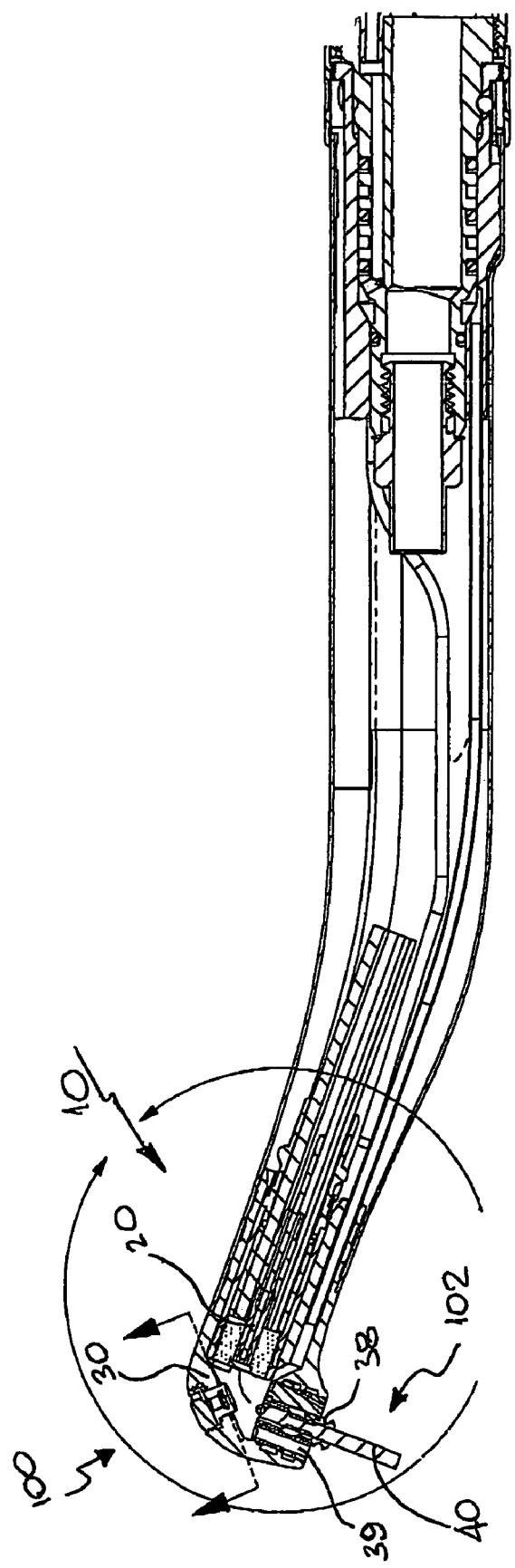
FIG. 2 is a sectional view of the illumination device of FIG. 1.

Although in certain embodiments of the invention, apparatus 10 may be useable in a person's hand or other suitable holding device to direct light toward a target surface, in the illustrated embodiment, illumination device 10 is configured to be coupled to a hand piece 100 (see FIG. 2). Hand piece 100 is structured to be held in a user's hand. Hand piece 100 is illustrated as having a contra-angle design configuration, including a hand piece output end 102 oriented at an angle to the output end of illumination device 10. In the illustrated embodiment, hand piece output end 102 is oriented at an approximately ninety degree angle to the output end of illumination device 10. To direct the emitted light from fibers 16 and 20 toward hand piece output end 102, a reflector 30 is provided with hand piece 100. Reflector 30 is illustrated as including a plurality of mirrors 32 and 34. In additional embodiments, fewer or more mirrors may be provided. Mirror 32 is illustrated as being configured to alter the light emitted from fiber 20. In other words, mirror 32 is configured to direct for example a beam generated by an erbium laser source from the output end of illumination device 10 to hand piece output end 102. Mirror 34 is illustrated as being configured to alter the path of light emitted from one or more fibers 16. In other words, mirror 34 is configured to direct one or more beams of light, such as blue light or white light, from the output end of illumination device 10 to hand piece output end 102. In addition, mirror 34 is configured to direct light 64 that is reflected back from the target surface toward fibers 18 to provide a signal that can be used for analysis, as discussed above.

Hand piece 100 is also illustrated as including a tip 40 to direct light emitted from fiber 20 toward a target surface as indicated by reference number 62. In addition, a sleeve 38 may be provided with hand piece 100 substantially surrounding tip 40. Sleeve 38 is illustrated as being made of a material that is substantially transparent to permit light emitted from fibers 16, such as white light, to be directed to a target surface, as indicated by reference number 60. Tip sleeve 38, as illustrated in FIG. 2, is mounted into the ferrule 39, which has multiple openings for optical waveguides to transmit light 60. In other embodiments the tip sleeve 38 may be constructed of transparent material such as sapphire or clear plastic. Light 60 may be used for example to illuminate the target surface. The illumination of the target surface may occur continuously during the procedure being performed, or the illumination may be interrupted. In addition, the illumination may be automatically or manually controlled. Mirrors 32 and 34 may also be constructed to focus one or more of the light beams into tip 40. In the illustrated embodiment, mirror 32 is constructed to focus the erbium laser beam emitted from fiber 20 into tip 40, and mirror 34 is constructed to focus the light emitted from fibers 16, such as blue light, white light, or other light, into ferrule 39 or sleeve 38.

Hand piece 100 may also include another tip structure 36, such as a curing tip, as illustrated in FIG. 1. Tip structure 36 can be used instead of tip 40, or in conjunction with tip 40. When tip structure 36 is a curing tip, the curing tip is positioned in hand piece 100 and configured to receive or collect blue light emitted from fibers 16 to direct the blue light toward a target surface to obtain a desired effect, such as curing of dental composites. To increase the amount of blue light that is collected by tip structure 36, a diameter can be chosen for tip structure 36 to maximize the amount of blue light collected. Tip 40 and tip structure 36 are preferably made of a sapphire or glass materials, including plastic materials, that is/are optically transparent to permit the light to be effectively transmitted therethrough to a target surface.

Figure 3:
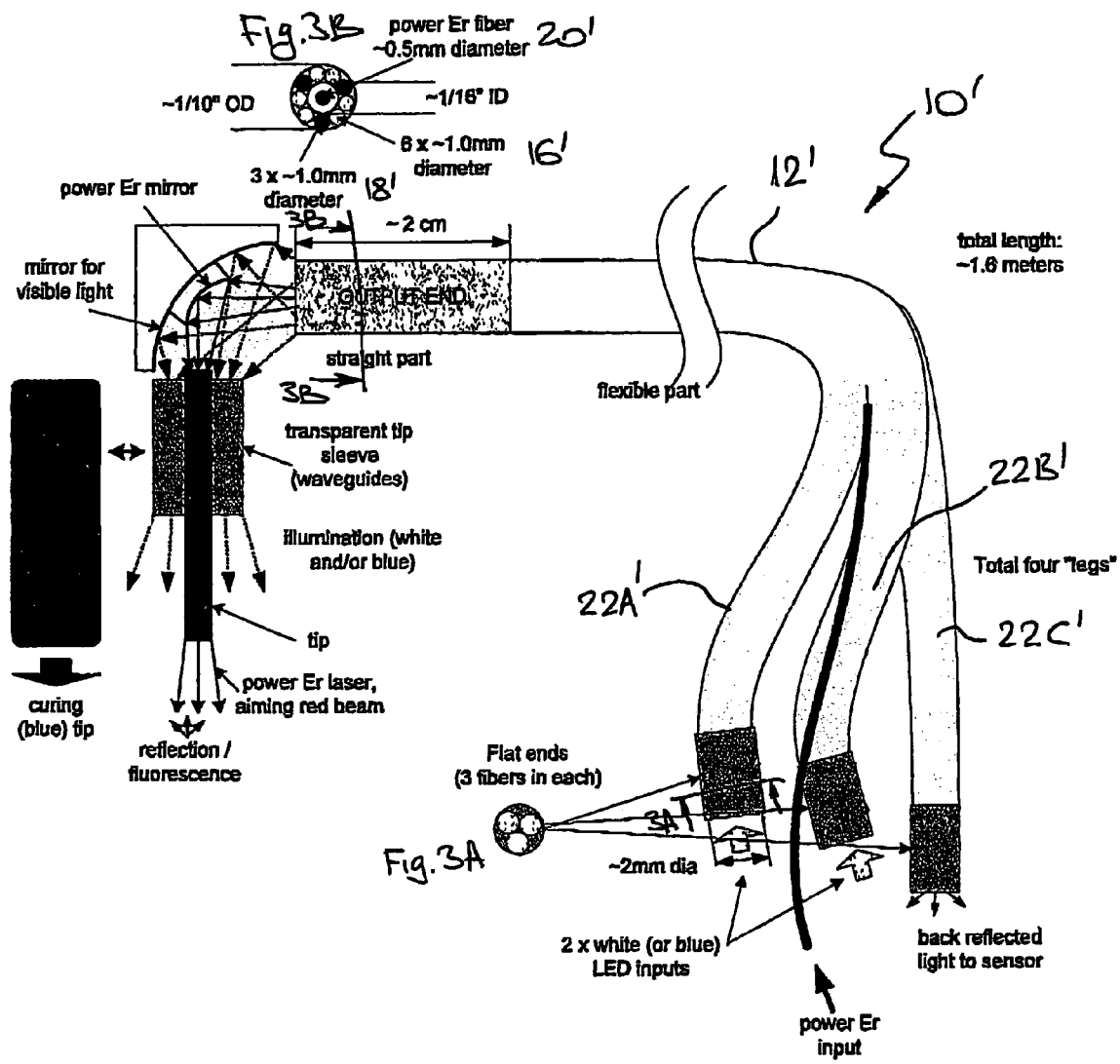
FIG. 3 is a side elevation view of an illumination device similar to the illumination device of FIG. 1.
Figure 4:
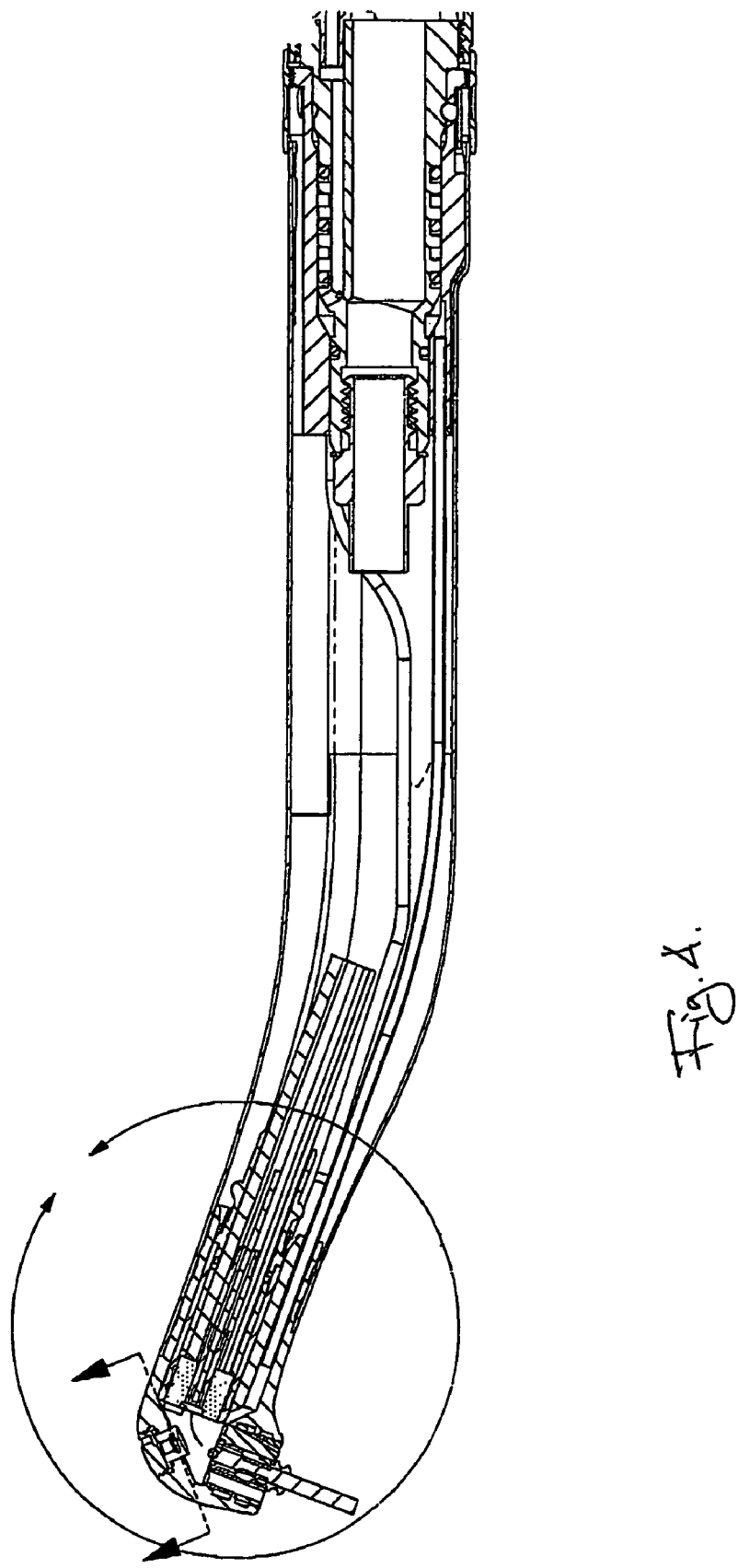
FIG. 4 is a sectional view of the illumination device of FIG. 3.

One particular, non-limiting embodiment of the invention is illustrated in FIGS. 3 and 4. In the embodiment shown in FIGS. 3 and 4, like parts are reflected by like numbers, and parts that are similar to the elements identified in the embodiment of FIGS. 1 and 2 have been identified by an apostrophe after the reference number. In the embodiment of FIGS. 3 and 4, the total length of illumination device 10' is between about 1 and about 2 meters. In one particular embodiment, illumination device 10' is about 1.6 meters long. Each proximal member 22A' and 22B' has a diameter between about 2 mm and about 3 mm, and preferably about 2.5 mm. Proximal members 22A', 22B', and 22C' meet to define a unitary tubular structure having an outer diameter between about 3 mm and about 5 mm, for example about 4 mm. Proximal members 22A', 22B', and 22C' are arranged so that the fibers contained therein define a central lumen having a diameter ranging from about 1 mm to about 2 mm, for example, about 1.5 mm (or about $\frac{1}{16}$ of an inch). This central lumen is structured to accommodate the power erbium laser fiber, such as fiber 20', which is similar to fiber 20 discussed above. In the embodiment illustrated in FIG. 3, proximal members 22A', 22B', and 22C' come together to form a unitary structure at a distance of approximately 5 cm from the proximal end of elongate body 12'. As shown in FIG. 3B, power erbium fiber 20' has a diameter of approximately 0.5 mm, fibers 16' have a diameter of about 1 mm, and fibers 18' have a diameter also of about 1 mm. The output end of illumination device 10' includes a substantially rigid, straight portion that is approximately 2 centimeters in length. Illumination device 10' includes six larger diameter fibers 16' concentrically arranged about a central lumen, and three fibers 18' concentrically arranged about a central lumen and equally spaced of elongate body 12', as shown in FIG. 3B. The numerical apertures of fibers 16' and 18' are about 0.51.

Similar to the embodiment shown in FIG. 1 and FIG. 2, light provided by two high power white LEDs is directed into proximal members 22A' and 22B' of FIG. 3. The white light may be used to illuminate the operational area. Each white light LED has a power of approximately ½ watt. One suitable example of a high-power white LED is a Luxeon Emitter, 5 W (Model No. LXHL-PW03). An erbium laser fiber is placed inside a central lumen created by the fibers in proximal members 22A', 22B', and 22C', as discussed above.

By way of the disclosure herein, an illumination device has been described that utilizes electromagnetic energy to affect a target surface. In the case of dental procedures, the illumination device includes an optical fiber for transmitting laser energy to a target surface for treating, e.g., ablating, a dental structure, such as a tooth, a plurality of optical fibers for transmitting for example white light to a tooth to provide illumination of the target surface, a plurality of optical fibers for transmitting blue light for illumination curing, whitening, and/or diagnostics of a tooth, and a plurality of optical fibers for transmitting light from the target surface back to a sensor for analysis. In the illustrated embodiment, the optical fibers that transmit white light also may transmit blue light. In accordance with one aspect of the invention herein disclosed, an illumination device comprises an illumination tube having a feedback signal end and a double mirror hand piece.

In certain embodiments, the methods and apparatuses of the above embodiments can be configured and implemented for use, to the extent compatible and/or not mutually exclusive, with existing technologies including any of the above-referenced apparatuses and methods and including those disclosed in any of the following patents: U.S. Pat. Nos. 5,741,247; 5,785,521; 5,968,037; 6,086,367; 6,231,567; 6,254,597, 6,288,499; 6,350,123; 6,389,193; and 6,544,256, all of which are commonly assigned and the entire contents of which are incorporated herein by reference.

While this invention has been described with respect to various specific examples and embodiments, it is to be understood that the invention is not limited thereto and that it can be variously practiced with the scope of the following claims. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

The invention claimed is:

1. A handpiece, comprising:
an illumination device comprising an elongate body having a device distal end, a device proximal end, a device axis extending between the device distal end and the device proximal end, and a hollow interior dimensioned to accommodate a plurality of light transmitters, the proximal end of the elongate body including at least two proximal members, each proximal member having a hollow interior to accommodate at least one light transmitter and in communication with the hollow interior of the elongate body so that the at least one light transmitter extends from the proximal end of the elongate body to the distal end of the elongate body, the plurality of light transmitters comprising a power optical fiber having a first transmitting interior coupled to a laser generator and an illumination optical fiber having a second transmitting interior that differs from the first transmitting interior;
an output tip comprising a first output tip waveguide having a laser-transmitting interior and configured to receive laser light from the power optical fiber and further comprising a second output tip waveguide having an illumination transmitting interior, which is not the same as the laser transmitting interior, and configured to receive visible light from the illumination optical fiber, the output tip being constructed to direct the laser light and the visible light away from an output end of the handpiece; and
an optical element positioned in a vicinity of the device axis and the device distal end, the optical element being configured to receive light from the power optical fiber and to direct light from the power optical fiber into the first output tip waveguide, and the optical element further being configured to receive light from the illumination optical fiber and to direct light from the illumination optical fiber into the second output tip waveguide.

2. The apparatus as set forth in claim 1, wherein the at least two proximal members comprises three optical fibers.

3. The apparatus as set forth in claim 1, wherein, in a vicinity of the distal end, the at least two proximal end members form a hollow interior dimensioned to accommodate at least one optical fiber.

4. The apparatus as set forth in claim 1, wherein:
the at least two proximal members comprises a first proximal member, a second proximal member, and a third proximal member;
the first proximal member, the second proximal member and the third proximal member each have an equal inner diameter; and
the proximal end of the elongate body further includes a fourth proximal member having an inner diameter smaller than the inner diameter of the first proximal member and the second proximal member.

5. A handpiece, comprising:
an illumination device comprising an elongate body having a distal portion and a proximal portion, the distal portion comprising a unitary distal portion tube having a lumen, and the proximal portion including a plurality of proximal portion tubes, each proximal portion tube having a lumen in communication with the lumen of the distal portion tube of the elongate body;
a power optical fiber having a first transmitting interior coupled to a laser generator, a proximal end in a vicinity of a first one of the proximal portion tubes, and a distal end in a vicinity of the lumen and the distal portion;
an illumination optical fiber having a second transmitting interior that differs from the first transmitting interior, a proximal end in a vicinity of a second one of the proximal portion tubes, and a distal end in a vicinity of the lumen and the distal portion;
an optical element positioned to intercept laser light from the power optical fiber and to direct the laser light in a direction toward a handpiece output end, the optical element further being positioned to intercept illumination light from the illumination optical fiber and to direct the illumination light in a direction toward the handpiece output end;
a first output tip waveguide having a laser-transmitting interior and configured to receive laser light from the power optical fiber and to direct the laser light away from the handpiece output end; and
a second output tip waveguide having an illumination transmitting interior, which is not the same as the laser transmitting interior, and configured to receive visible light from the illumination optical fiber and to direct the visible light away from the handpiece output end.

6. The device as set forth in claim 5, wherein the distal portion and proximal portion of the elongate body are integrally formed.

7. The device as set forth in claim 5, and further comprising a first, a second, a third, and a fourth proximal portion tube.

8. The device as set forth in claim 7, wherein three of the four proximal portion tubes have similar diameters.

9. The device as set forth in claim 7, wherein the first, second and the third proximal portion tubes each contain three optical fibers disposed in the lumen of the respective proximal portion tubes, and the fourth proximal portion tube contains one optical fiber disposed in the lumen of the fourth proximal portion tube.

10. The device as set forth in claim 9, wherein each of the first and second proximal portion tubes contains a plurality of optical fibers fused together.

11. The device as set forth in claim 5, wherein the elongate body is about 1.5 meters in length and the proximal portion of the elongate body is about 5 centimeters in length.

12. The device as set forth in claim 5, wherein the distal portion and the proximal portion are made of a flexible material.

13. The device as set forth in claim 5, wherein the distal portion includes a region that is rigid and straight relative to the proximal portion of the elongate body.

14. The device as set forth in claim 5, wherein the distal portion includes a light emitting output end, and the device further comprises at least one mirror distally located to the light emitting output end.

15. The device as set forth in claim 14, comprising a first mirror constructed to reflect electromagnetic energy provided by an erbium laser, and a second mirror constructed to reflect visible light.

16. The device as set forth in claim 14, wherein the hand piece is dimensioned to be held by a user's hand, the hand piece comprising an output tip, which includes the first output tip waveguide and the second output tip waveguide and which is coupled to the distal end of the elongate body to direct electromagnetic energy from the hand piece.

17. The device as set forth in any of claims 1-16, wherein the device farther comprises a fluid output for directing fluid toward a target surface when electromagnetic energy is directed from the hand piece.

18. The device as set forth in claim 17, wherein the fluid comprises atomized fluid particles emitted from the fluid output above the target surface so that in use portions of the atomized fluid particles intersect the laser light above the target surface.

19. The device as set forth in claim 18, wherein the target surface comprises one of bone, teeth, cartilage and soft tissue and the atomized fluid particles comprise water.

20. The device as set forth in claim 18, wherein the laser light is configured to impart relatively large amounts of energy into the atomized fluid particles in the volume above the target surface to thereby expand the atomized fluid particles and impart disruptive forces onto the target surface.

21. The device as set forth in claim 20, wherein:

the fluid output is configured to place water into the volume; and the device comprises one of an Er:YAG, an Er:YSGG, an Er, Cr:YSGG and a CTE:YAG laser.

\* \* \* \* \*